United States Patent [19]
Gretillat et al.

[11] Patent Number: 5,545,567
[45] Date of Patent: Aug. 13, 1996

[54] LUMINOSCOPIC ANALYTIC DEVICE AND METHOD

[75] Inventors: François Gretillat, Neuchâtel; Jean-Paul Pellaux; John M. Hale, both of Geneva; Eugen Weber, Hinwil, all of Switzerland

[73] Assignee: Orbisphere Laboratories Neuchatel S.A., Neuchatel, Switzerland

[21] Appl. No.: 443,421

[22] Filed: May 18, 1995

[30] Foreign Application Priority Data

Jun. 4, 1994 [EP] European Pat. Off. ............. 94810331

[51] Int. Cl.⁶ .................................................. G01N 21/64
[52] U.S. Cl. ................... 436/172; 422/82.06; 422/820.7; 422/82.08; 250/458.1; 250/459.1
[58] Field of Search ............................ 422/82.05, 82.06, 422/82.07, 82.08, 820.9; 436/172; 250/458.1, 459.1

[56] References Cited

U.S. PATENT DOCUMENTS

| Re. 31,879 | 5/1985 | Lübbers et al. |
|---|---|---|
| 4,817,413 | 4/1989 | Asano et al. |
| 4,889,690 | 12/1989 | Opitz et al. |
| 4,980,278 | 12/1990 | Yamada et al. |
| 5,030,420 | 7/1991 | Bacon et al. |
| 5,037,968 | 8/1991 | Simon et al. |
| 5,268,305 | 12/1993 | Ribi et al. ............................ 422/82.09 |
| 5,272,090 | 12/1993 | Gavish et al. ........................ 422/82.08 |

FOREIGN PATENT DOCUMENTS

| 0083703 | 7/1983 | European Pat. Off. |
|---|---|---|
| 0127106 | 12/1984 | European Pat. Off. |
| 0281829 | 9/1988 | European Pat. Off. |
| 0106086 | 5/1974 | Germany. |

*Primary Examiner*—Jeffrey R. Snay
*Attorney, Agent, or Firm*—Wigman, Cohen, Leitner & Myers, P.C.

[57] ABSTRACT

An analytic device (1) for reflective luminoscopy comprises within an enclosure (11): a light source (12); a pair of spaced light detectors (141, 142); and a refractor body (16); the refractor body comprises a planar base (161), an entry plane (163) near the light source for light emanating therefrom, and an exit plane (165) near the spaced detectors for light that is being sensed by at least one of the detectors; the entry plane and the exit plane enclose an angle of less then 180° and not less than 90°, the enclosure further includes a light-collimating means or lens (13) between the light source and the entry plane; a light-collecting means or lens (15) between the light detectors and said exit plane, and at least one light-reflecting surface (171) near the planar base (161); at least one luminoscopic layer (191) normally comprising a luminoscopic indicator and a thin transparent carrier, is arranged between the planar base and the at least one light-reflecting surface; the device includes both a luminoscopic reference as well as a measuring area for a luminoscopic reaction between a luminoscopic layer and a species of analytic interest.

8 Claims, 3 Drawing Sheets

Fig. 1

LUMINOSCOPIC ANALYTIC DEVICE AND METHOD

BACKGROUND OF THE INVENTION

1. Field of the invention

This invention relates generally to the art of luminoscopic analysis and specifically to an analytic device and method for use in reflective luminoscopy.

The terms "luminoscopic" and "luminoscopy" are used herein synonymously with "luminometric" and "luminometry", respectively, and are intended to encompass "colorimetric" and "colorimetry", as well as "fluorometric" and "fluorometry", respectively. "Colorimetry" and "colorimetric" are understood herein as involving measurement of color changes in response to an analytic sample containing a substance of analytic interest "Fluorometry" and "fluorometric", on the other hand, is intended to refer to methods and devices where a change of fluorescence is measured in response to a substance of interest contained in an analytic sample.

More specifically, the invention concerns a device for use in reflective luminoscopy, i.e. where luminoscopic changes are observed by a reflected beam of light, preferably of an essentially monochromatic nature; for brevity, such a device will also be called a "reflectoscope" herein.

Further, the term "luminometric layer" as used herein is intended to refer to an essentially transparent layer of a solid or pseudo-solid (e.g. gel-type) material containing a colorimetric or fluorometric indicator.

2. Prior Art

Luminoscopy is known in the analytic art and specific examples can be found in EP-A-0 083 703, EP-A-0 127 106, EP-A-0 281 829 and the art of reference discussed in these documents. Reflective luminoscopy is disclosed in the first of the above documents. This method has the inherent advantage that observation can be made from one side of the luminoscopic layer while interaction of such layer with the substance or species of analytic interest acts upon the layer from the opposite side; in other words, the luminoscopic reaction between the indicator and the species of analytic interest can be carried out in a relatively simple manner without interfering with the observation of the result of the luminoscopic reaction.

OBJECTS AND SUMMARY OF THE INVENTION

Applicants' research leading to the present invention has shown that a main disadvantage of prior art methods is the lack of uniform conditions when comparing the luminoscopic layer that interacts with a species of analytic interest with a reference layer.

Accordingly, it is a main object of the invention to provide for a reflectoscope that permits safe and reproducible correlation of the results of a luminoscopic reaction , i.e. change of color or fluorescence in response to the species of analytic interest.

This object is achieved according to a first embodiment of the invention by an analytic device for reflective luminoscopy, or reflectoscope, comprising within an enclosure: a light source, e.g. of a "punctiform" rather than planar type, such as an incandescent lamp emitting monochromatic light or a laser; a pair of spaced light detectors (also termed "dual detector"); a refractor body comprising a planar base, an entry plane near the source for light emanating therefrom, and an exit plane near said spaced detectors for light that is being sensed by said detectors, said entry plane and said exit plane enclosing an angle of less then 180° and not less than 90°, a light-collimating means between said light source and said entry plane; a light-collecting means, e.g. a collector lens, between the light detectors and the exit plane, at least one light-reflecting surface near the planar base of the refractor; and at least one or first luminoscopic layer between said planar base and said at least one light-reflecting surface.

BRIEF DESCRIPTION OF PREFERRED EMBODIMENTS OF THE INVENTION

As will be explained in more detail below, the reflectoscope according to the invention permits simultaneous observation of a luminoscopic reaction and a luminoscopic reference under otherwise identical conditions.

Thus, according to a preferred embodiment, the reflectoscope according to the invention includes two different luminoscopic layers, one of which is the reference layer while the other is the measuring layer. These layers can be arranged in a coplanar manner side-by-side between the refractor base and a reflecting surface, e.g. a mirror for total reflection.

For many purposes of the invention it is preferred, however, that the reference layer and the measuring layer are arranged in different planes parallel to the base plane of the refractor. The term "near" as used herein to refer to a spatial relation is not limited to a directly adjacent position but includes the presence of an intermediate space, or the use of one or more transparent intermediate layers for separation, support and the like.

According to a second embodiment the invention provides for a method
of analytic reflective luminoscopy comprising providing within an enclosure:
a light source;
a pair of spaced light detectors;
a refractor body;
said refractor body comprising a planar base, an entry plane near said light source for light emanating therefrom, and an exit plane near said spaced detectors for light that is being sensed by said detectors, said entry plane and said exit plane enclosing an angle of less then 180° and not less than 90°,
a light-collimating means between said light source and said entry plane,
a light-collecting means between said light detectors and said exit plane,
at least one light-reflecting surface near said planar base, and
at least one or first luminoscopic layer between said planar base and said at least one light-reflecting surface;
said layer comprising a reference portion where no luminoscopic reaction occurs, and a measuring portion where a species of analytical interest interacts with said luminoscopic layer.

BRIEF DESCRIPTION OF THE DRAWINGS

The invention will now be explained in more detail with reference to the enclosed drawings in which.

DETAILED DESCRIPTION OF THE PREFERRED EMBODIMENTS

Figure 1:
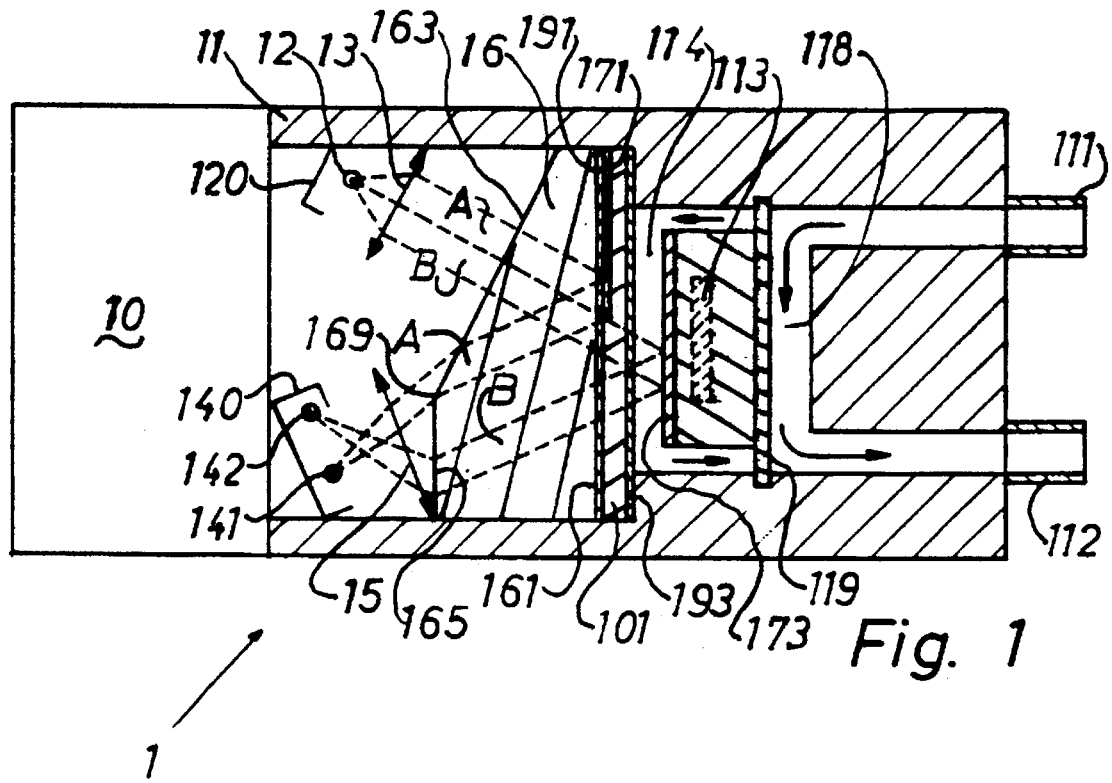
FIG. 1 is a diagrammatic sectional view of a reflectoscope according to the invention.

Device 1 of FIG. 1 is a simplified and diagrammatic sectional view of a reflectoscope according to the invention in a preferred embodiment. Enclosure 11, e.g. in the form of an essentially cylindrical housing made of a suitable inorganic or organic material, e.g. stainless steel, synthetic resin or a ceramic material, includes a conventional light source 12 capable of emitting substantially monochromatic light per se or being combined with a filter suitable for producing such monochromatic radiation in the visible spectrum. Shielding means 120 are optional.

Figure 2:
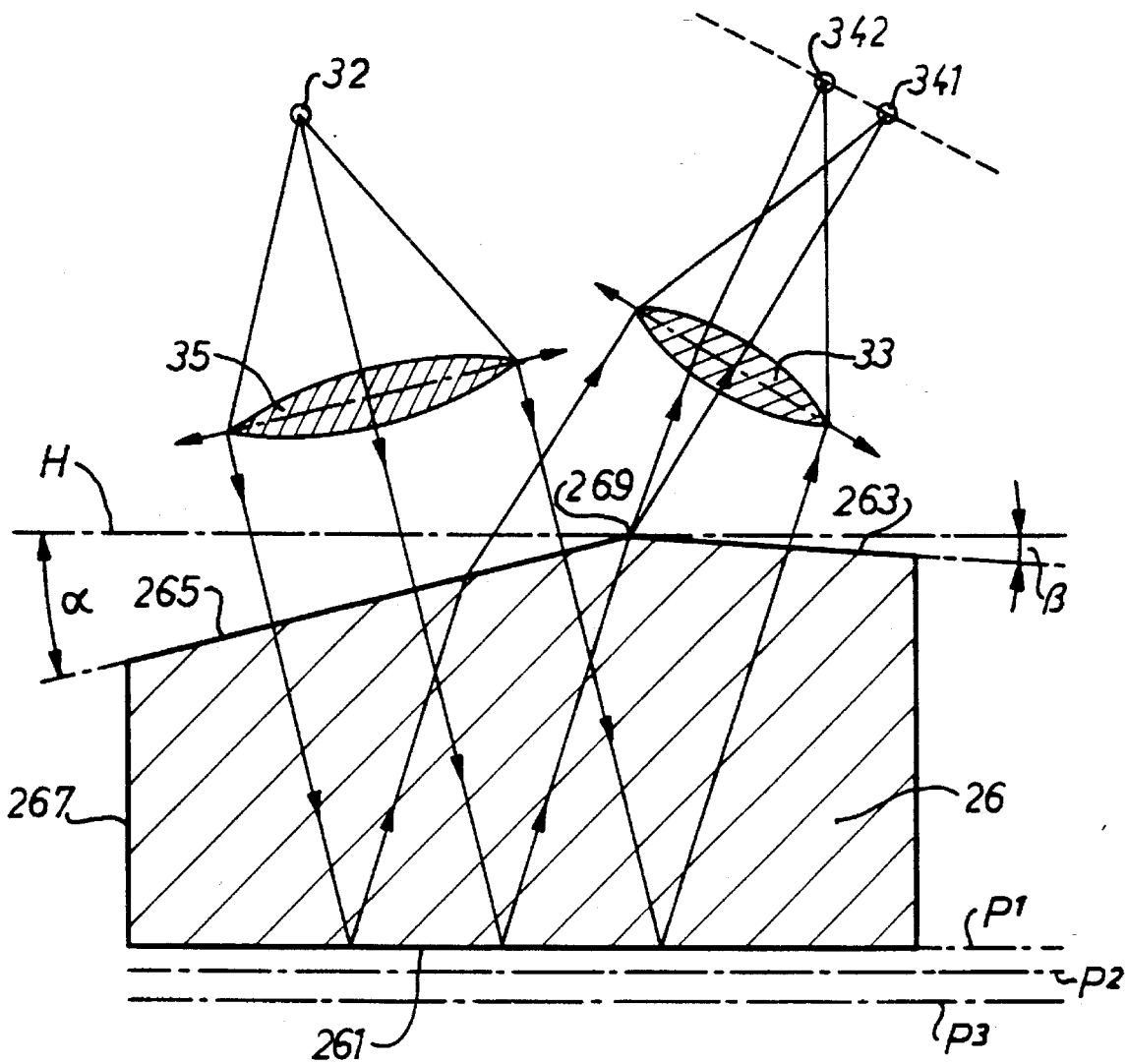
FIG. 2 is a diagrammatic sectional view of the refractor for a refelctoscope according to the invention.

The divergent light being emitted by light source 12 passes a conventional light collimating means 13, e.g. a collimating lens, and then enters at an angle of 90° into refractor body 16 made of a mineral or organic glass of a quality known to be suitable for optical purposes and having a suitable refractive index, e.g. in the range of from about 1.2 to 1.6. The optical effectiveness of the refractor body is determined, in essence by the angular orientation of entry plane 163 and exit plane 165 relative to base plane 161 and the refractive index of the material of refractor body 16. With reference to FIG. 2 showing a diagrammatic sectional view of the refractor body 26 (the first digit indicating the number of the Figure in question while the second digit indicates the same or a similar parts where possible) where planes 163 or 263, and 165 or 265 include an angle of less then 180° and not less than 90°, e.g. 170°–150°, e.g. about 167°.

Preferably, both angles $\alpha$ and $\beta$ include an angle with the horizontal H and, in any case form an apex 169, 269. All surfaces 161,261; 163,263; and 165,265 are ground and polished to optical clarity and transparency while cylindrical side face 267 preferably is matted. Planes $p^1$, $p^2$, and $p^3$ are indicated in FIG. 2 to show possible positions of adjacent layers which might be of the transparent intermediate type or constitute the planes of luminoscopic layers and reflective layers or mirrors.

Returning to FIG. 1, the essentially parallel beam emanating from collimating means 13 and consisting of two portions A and B passes through entry plane 163, through base plane 161 and a first luminoscopic layer, e.g. a thin transparent reference layer containing an optically clear carrier, such as an organic polymer film, in which the luminoscopic or colorimetric indicator for the analytic species of interest is molecularly dispersed. Essentially half of the parallel beam, or portion A is reflected by a mirror layer 171 on a transparent support 101, e.g. applied as a thin layer, such as by vacuum deposition methods; beam portion A reflected by mirror 171 passes upwards through refractor body 16 and exits through the portion of the original entry plane 163 adjacent apex 169. This reflected beam portion A is now refracted at an angle $\tau^1$ and then passes through light collecting means 15, e.g. a collector lens, so as to be focused at the site of detector 141, 241 where it produces a first or reference signal that is passed (conduit not shown) into an integrated signal processor shown generally as 10. Structure and operation of such processors are well known in the art and need not be explained in more detail herein.

The second portion B of the parallel beam emanating at the collimating means 13 passes reference layer 191 and enters into transparent support layer 101 from where it continues through a second luminoscopic layer 193 which is the layer that interacts with the analytic species of interest. Such interaction is caused at the interface of layer 193 and the species of analytic interest passing through a space or chamber 114.

In a typical application according to the invention a fluid medium, e.g. an aqueous process stream, passes via inlet 111 through a space or chamber 118 within enclosure 11 and exits at outlet 112. A separator means 119 is permeable for gaseous fluids but not for liquids, such as a separator membrane commercially available under the trade mark Gorerex and having a typical thickness in the range of from about 50 to 250 µm. Thus, only the gaseous constituents of the liquid process stream will reach chamber 114 and react with luminoscopic layer 193, i.e. the colorimetric or fluorometric indicator dispersed therein. Beam portion B is then reflected by a second mirror 173 positioned within chamber 114.

Preferably, a heating means 113, e.g. an electric resistor, is in thermal connection with mirror 173 so as to avoid condensation on the surface thereof. Energy can be supplied to the heating means via conduits (not shown), or by induction or the like.

Beam portion B after reflection on mirror 173 passes through space 114, reactive layer 193, support layer 101, reference layer 171, and through refractor body 16 so as to exit therefrom through exit plane 165. Beam portion B is refracted upon entry into the gaseous phase, normally air, and passes collector means 15 so as to focus at the site of the second light detector 142.

Dual detectors 141, 142 of an analytic device according to the invention are spaced by an appreciable distance of typically in the range of from 1–10 mm, preferably 2–6 mm, in dependence of the design of device 1 and its components. Obviously, a main design parameter of the embodiment illustrated in FIG. 1 is defined by the end of first mirror 17 and the corresponding "edge" of beam a (the reference beam).

It is well within the teaching of the present invention that reference layers 171 and 193 are arranged in a common plane so that one portion of the layer is in contact with the analytic species of interest for luminoscopic reaction while the other portion is isolated against the analytic species so as to remain as reference. In such an embodiment, the mirrors could also be coplanar in that the mirror below the reference portion of the luminoscopic layer would be distanced from the reference layer portion by a transparent layer of the same thickness as the distance defined by the thickness of the space or chamber 114. However, such an embodiment is not particularly preferred herein.

Figure 3:
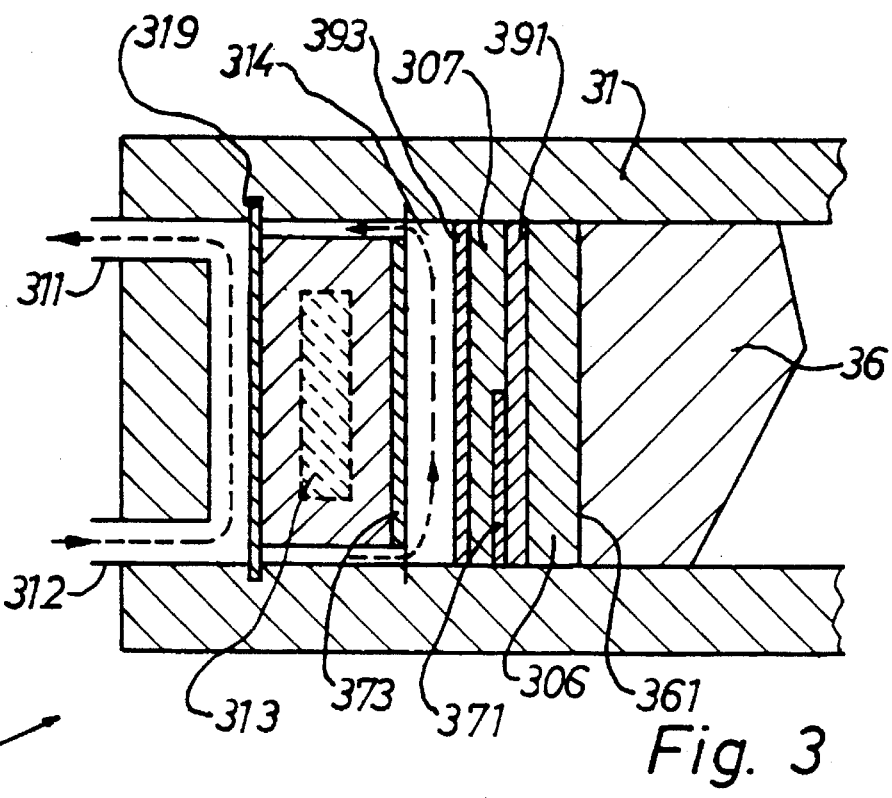
FIG. 3 is a diagrammatic sectional view showing the reference and measuring portion of a reflectoscope according to the invention in more detail.

The diagrammatic sectional view of FIG. 3 illustrates the broken-away portion of a reflectoscope according to the invention showing another layer arrangement between the bottom plane 361 of refractor body 36 and the end of enclosure 31 provided with inlet 311 and outlet 312 for a liquid sample.

A first support plate 306 made of optical glass (mineral or organic) is arranged adjacent of refractor body 36. A thin film (not shown) of an optical oil can be used for improved optical homogeneity in a manner known per se in the optic art. Luminoscopic layer 391 serving as reference layer is positioned between first support plate 306 and a second support plate 307 made of the same material as plate 306.

A mirror, e.g. a thin metal layer applied onto half of plate 306, e.g. by vapor deposition serves as the first reflective surface 371. It should be noted that the thicknesses of the films, layers, mirrors etc. shown in FIGS. 1 and 3 are greatly exaggerated for illustration purposes, and no conclusion should be drawn from the dimensions or dimensional ratios depicted in FIGS. 1 and 3. As a matter of practice, support plates can have substantial thicknesses, e.g. in the range of from about 1 to about 20 mm while the luminoscopic layers will be "thin", e.g. in the typical range of from about 5 to about 50 μm, while the reflective surfaces or mirrors can be "very thin", i.e. as thin as feasible for stable operation, e.g. below 1 μm.

The second luminoscopic layer 393 is connected with the second support plate 307 and is in contact with the analytic species of interest (separated from a processing stream by a separator means 319 as explained above) and forms part of a chamber 314 comprising a mirror surface 373. Again, a heater 313 can used to prevent condensation on the surface of mirror 373.

Figure 4A:
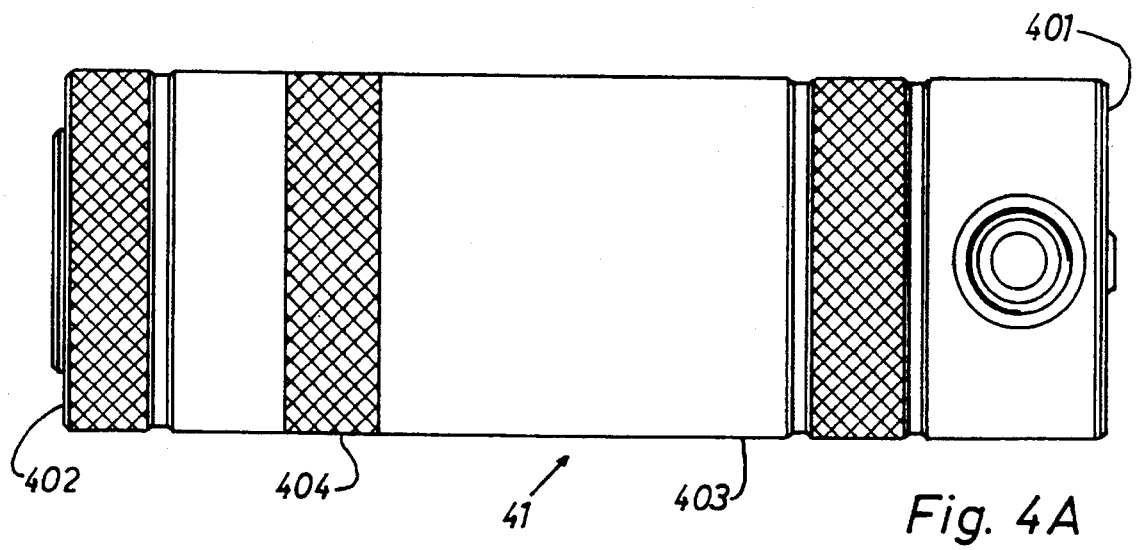
FIGS. 4A and 4B show a side view and a sectional view of a reflectoscope according to the invention in a semi-diagrammatic manner.
Figure 4B:
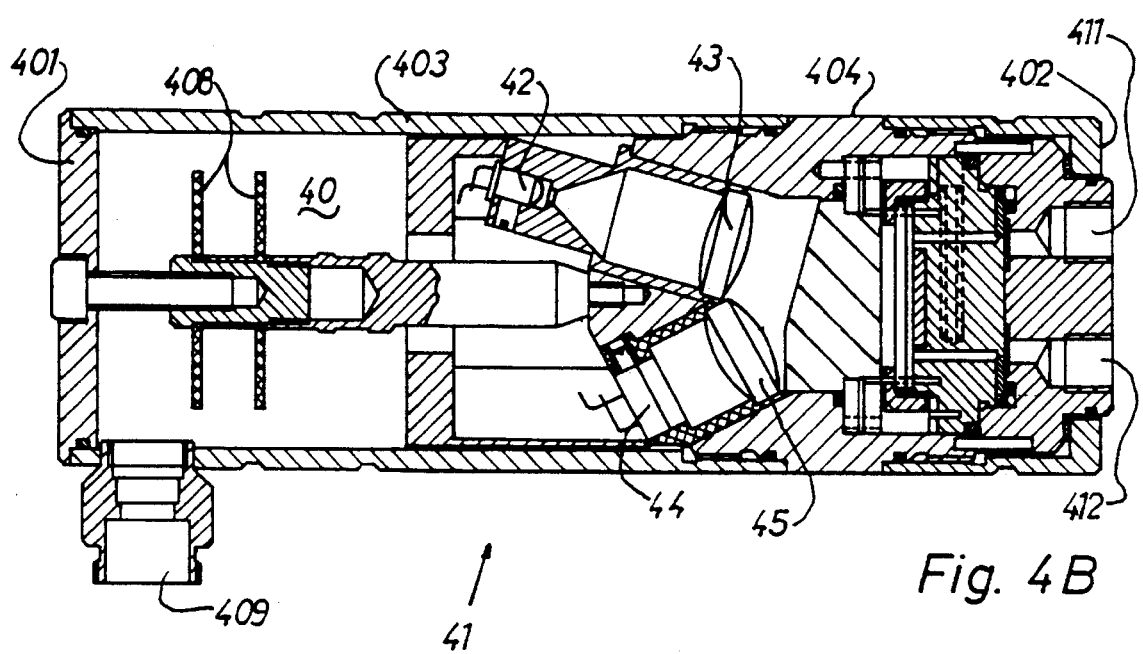

FIGS. 4A and 4B show a side view and a sectional view, respectively, of a reflectoscope 4 according to the invention in a semi diagrammatic and partially simplified illustration.

Enclosure 41 is in the form of a housing consisting of a top plate 401 internally supporting the integrated signal processor 40, e.g. on plates 408. Top plate 401 is secured to an upper sleeve 403 threadingly connected with a block portion 404 with bottom portion 402 with inlet/outlet means 411, 412.

Light source 42, collimator 43, detectors 44, collector 45 and refractory body 46 are essentially as explained above and do not require additional explanation.

Also, luminoscopic operation of the reflectoscope with various analytic species needs no further explanation or exemplification in that a large number of such operations as well as fluorometric and colorimetric indicators, carriers for the luminoscopic layers and further details can be found in the above mentioned references as well as in the art of record cited in the said documents.

Hence various modification of the reflectoscope of the present invention will be apparent to those experienced in the art and the above illustrations are not to be understood as limitations and it will be appreciated that many modifications and variations of the present invention are within the purview of the appended claims without departing from the spirit and intended scope of the invention.

What is claimed is:

1. An analytic device for reflective luminoscopy comprising within an enclosure:

a light source;

a pair of spaced light detectors;

a refractor body;

said refractor body comprising a from surface which forms an entry plane and an exit plane, said entry and exit planes enclosing an angle of less than 180° and not less than 90°, and a rear surface which forms a base plane, said light source and light detectors being positioned adjacent the front surface of said refractor body, a light-collimating means between said light source and said entry plane, a light-collecting means between said light detectors and said exit plane, a first light-reflecting layer positioned adjacent said base plane, a first luminoscopic layer positioned between said base plane and said first light-reflecting layer, said first light-reflecting layer being constructed and positioned so as to reflect only a portion of light emanating from said light source which is passed through said refractor body and said first luminscopic layer, said first luminoscopic layer serving as a reference layer, a second light-reflecting surface constructed and positioned so as to reflect light emanating from said light source which is passed through said refractor body, said first luminoscopic layer, and is not reflect by said first light-reflecting layer, a second luminoscopic layer positioned between said first and second light-reflecting layers, said second luminosopic layer serving as a measuring area for reaction with a species of analytic interest which is in contact with said second luminoscopic layer, wherein light from said first reflecting layer is directed by said refractor body to a first of said light detectors and light from said second reflecting layer is directed by said refractor body to a second of said light detectors.

2. The device of claim 1 wherein said each luminoscopic layer is a transparent membrane containing a colorimetric or fluorometric indicator.

3. The device of claim 1 wherein said enclosure comprises a chamber for contacting said second luminoscopic layer, or portion thereof, with a species of analytic interest.

4. The device of claim 1 having inlet and outlet means for continuously or intermittently passing a fluid medium of analytic interest through said device.

5. The device of claim 4 wherein said fluid medium is a liquid and wherein a separating means is provided to separate a gaseous component from said fluid medium.

6. The device of claim 1 comprising means for separating a gaseous constituent containing a species of analytic interest from a fluid sample or process stream; and a chamber for contacting said gaseous constituent with a reactive luminoscopic layer; said chamber comprising a mirror and heating means in thermal contact with said mirror so as to prevent condensation thereon.

7. The device of claim 6 including a heater in thermal connection with said reflector.

8. An analytic method for reflective luminoscopy comprising the steps of:

providing light from a light source;

detecting light by a pair of spaced light detectors:

refracting light from said light source by a refractor body; said refractor body comprising a front surface which forms an entry plane and an exit plane, said entry and exit planes enclosing an angle of less than 180° and not less than 90°, and a rear surface which forms a base plane, said light source and light detectors being positioned adjacent the front surface of said refractor body, collimating said light by a light-collimating means between said light source and said entry plane, collecting light by a light-collecting means between said light detectors and said exit plane, reflecting light by a first light-reflecting layer positioned adjacent said base plane, providing a first luminoscopic signal by a first luminoscopic layer positioned between said base plane and said first light-reflecting layer, said first light-reflecting layer being constructed and positioned so as to reflect only a portion of light emanating from said light source which is passed through said refractor body and said first luminoscopic layer, said first luminoscopic layer serving as a reference layer, reflecting light by a second light-reflecting surface constructed and positioned so as to reflect light emanating from said light source which is passed through said refractor body, said first luminscopic layer, and is not reflected by said first light-reflecting layer, providing a second luminoscopic signal by a second luminoscopic layer positioned between said first and second light-reflecting layers, said second luminoscopic layer serving as a measuring area for reaction with a species of analytic interest which is in contact with said second luminoscopic layer, wherein light from said first reflecting layer is directed by said refractor body to a first of said light detectors and light from said second reflecting layer is directed by said refractor body to a second of said light detectors.

* * * * *